United States Patent
Müller-Pathle et al.

(10) Patent No.: US 8,834,413 B2
(45) Date of Patent: Sep. 16, 2014

(54) CONTROLLING A MOTOR OF AN INJECTION DEVICE

(75) Inventors: Stephan Müller-Pathle, Frankfurt am Main (DE); Christian Nessel, Frankfurt am Main (DE); Christoph Eissengarthen, Ginsheim (DE); Navid Durrani, Essen (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 40 days.

(21) Appl. No.: 13/582,289

(22) PCT Filed: Mar. 15, 2011

(86) PCT No.: PCT/EP2011/053832
§ 371 (c)(1),
(2), (4) Date: Jan. 17, 2013

(87) PCT Pub. No.: WO2011/113806
PCT Pub. Date: Sep. 22, 2011

(65) Prior Publication Data
US 2013/0204224 A1     Aug. 8, 2013

(30) Foreign Application Priority Data

Mar. 16, 2010   (EP) ..................... 10156668

(51) Int. Cl.
*A61M 5/20*     (2006.01)
*A61M 31/00*    (2006.01)
*A61M 5/172*    (2006.01)
*A61M 5/145*    (2006.01)
*A61M 5/315*    (2006.01)

(52) U.S. Cl.
CPC ....... *A61M 5/20* (2013.01); *A61M 2005/31588* (2013.01); *A61M 2205/332* (2013.01); *A61M 5/172* (2013.01); *A61M 5/31546* (2013.01); *A61M 5/31525* (2013.01); *A61M 2205/8212* (2013.01); *A61M 5/1452* (2013.01)
USPC ............................................ 604/67; 604/151

(58) Field of Classification Search
CPC ................... A61M 2205/33; A61M 2205/332; A61M 31/00; F04B 49/06
USPC .................... 604/67, 131, 151, 154; 417/44.2
See application file for complete search history.

(56) References Cited

U.S. PATENT DOCUMENTS

| 5,647,853 A * | 7/1997 | Feldmann et al. ............ 604/155 |
| 6,520,930 B2 * | 2/2003 | Critchlow et al. ............. 604/67 |
| 2003/0073954 A1 | 4/2003 | Moberg et al. |

FOREIGN PATENT DOCUMENTS

| EP | 0481376 A2 | 4/1992 |
| WO | 2005093533 A1 | 10/2005 |

OTHER PUBLICATIONS

International Preliminary Report on Patentability for Int. App. No. PCT/EP2011/053832, mailed Sep. 27, 2012.

* cited by examiner

*Primary Examiner* — Quynh-Nhu H Vu
(74) *Attorney, Agent, or Firm* — McDonnell Boehnen Hulbert & Berghoff LLP

(57) ABSTRACT

In order to improve the energy efficiency of an injection device 100, a current is caused to be applied to a motor 113 of the injection device 100, which is related to a signal from a force sensor 115. The signal represents a force that is applied by the motor 113 to a plunger 122 of a cartridge 121.

17 Claims, 5 Drawing Sheets

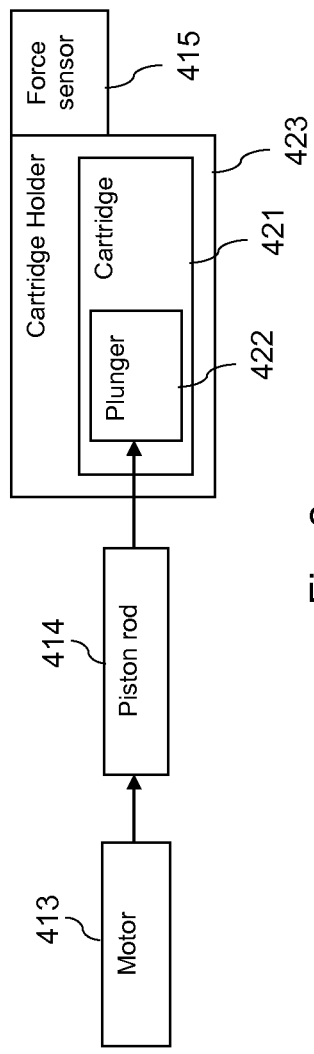
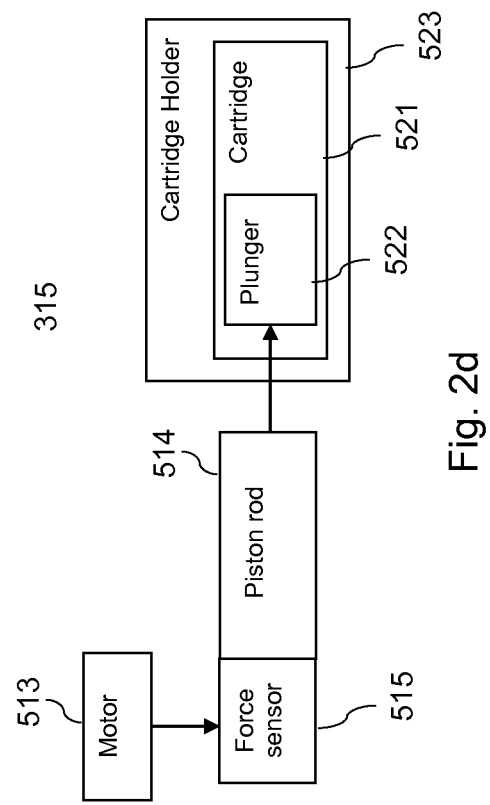

CONTROLLING A MOTOR OF AN INJECTION DEVICE

CROSS REFERENCE TO RELATED APPLICATIONS

The present application is a 35 U.S.C. 371 National Application of PCT/EP2011/053832 filed Mar. 15, 2011, which claims priority to European Patent Application No. 10156668.5 filed Mar. 16, 2010, and, the entire contents of which are incorporated entirely herein by reference.

FIELD OF THE INVENTION

The invention relates to the field of injection devices, and more specifically to the control of a motor of an injection device for a medicament.

BACKGROUND OF THE INVENTION

An injection device, for example an injection pen, can be driven electromechanically by using a motor, which drives a transmission to force a liquid substance out of a container.

The container may be a cartridge, for example for a medicament. The cartridge may have a cylindrical body made of glass, plastics, and/or the like. A first end of the cartridge may be closed by a septum which may be pierced by a needle. A second end of the cartridge may be closed by a plunger which is movable inside the cylindrical body of the cartridge to force out the liquid substance or medicament through the needle in the pierced septum.

With direct current motors, there is a direct relationship between the current consumption of the motor and the output torque. That is, the electrical power drawn by the motor is proportional to the mechanical power provided by the motor to a load. The rotation speed of the motor thus depends on the load and varies with changes in the load.

For injection devices, a stepper motor may be used instead of a direct current motor, since the rotation of the stepper motor can be controlled precisely. A stepper motor can be controlled to rotate by a selected number of steps regardless of the mechanical power taken off by the load. Since there is a direct relation between the amount of movement of a transmission driven by a motor and the amount of rotation of the motor, it is possible to drive a transmission in a sequence of steps and thereby to discharge a desired dose of the liquid substance.

A microcontroller may be employed for computing the number of steps required for achieving the desired dose and for generating corresponding control signals for the stepper motor.

The available torque of a stepper motor depends primarily on the provided current, while the rotation frequency only depends on the control signals provided to the motor. If less mechanical power is taken off at the motor shaft than could be provided by the motor, the excess power is converted into heat. In contrast to a direct current motor, there is thus no direct relation between the consumed electrical power and the provided mechanical power.

Generally, an electronic circuit is used to control a sequence in which coils of the stepper motor are energized to obtain a desired rotation, and the current is kept constant irrespective of the operating voltage and the rotation frequency. This means that usually more electrical power is used than required for the provided mechanical power.

As a result, the energy efficiency is not optimal. In particular in the case of battery driven devices, however, high energy efficiency is desirable to obtain a high durability of the batteries.

Document EP 0 481 376 A2 describes an apparatus for controlling a stepping motor that is used for driving a chemical pump. The apparatus includes a random access memory for storing a minimum current value required for driving the chemical pump at each of divisional intervals of one cycle of the chemical pump, two photo interrupters for sensing an angular location of the stepping motor corresponding to each of the intervals of the chemical pump, and a central processing unit connected to the two photo interrupters for controlling the stepping motor in accordance with the angular location of the stepping motor sensed by the two photo interrupters, the central processing unit being so arranged that it uses the minimum current value required for driving the chemical pump at an angular location following the angular location sensed by the two photo interrupters.

Document WO 2005/093533 A1 suggests modifying an electrical current value driving an infusion pump stepper motor in response to distal pressure information and other information. The distal pressure is a backpressure resisting the forward pressure generated by the infusion pump in applying medication intravenously. With a common type of pump, a plastic tube leading from a bag or bottle on a drip stand to the intravenous needle passes through a special gate in which it is occluded between a row of 'fingers' which are moved by a cam mechanism to squeeze the closed point forward.

SUMMARY OF THE INVENTION

A method is proposed, which comprises receiving a signal from a force sensor. The signal represents a force that is applied by a motor, for example a stepper motor, of an injection device to a plunger or bung of a cartridge. The method further comprises causing a current to be applied to the motor, which is related to the signal from the force sensor. That is, the current is controlled based on, or in response to, the signal from the force sensor. For example, the current may be derived from the force by multiplication with a factor. The current may further be increased by a fixed amount or by a fixed percentage.

Moreover, an apparatus is proposed, which comprises a controller. The controller is configured to receive a signal from a force sensor. The signal represents a force that is applied by a motor of an injection device to a plunger of a cartridge. The controller is further configured to cause a current to be applied to the motor, which is related to the represented force.

The apparatus could be implemented exclusively in hardware or in a combination of hardware and software. In the latter case, the controller could be for instance a microcontroller or any other kind of control unit that comprises a processor. The processor could then be configured to execute software implemented in the controller. The apparatus could comprise exclusively the controller or additional components. It could be for instance an injection device, an integrated circuit for an injection device or any other subunit of an injection device. Such a subunit could comprise in addition to the controller for instance at least one of a motor current driver which applies the current to the motor, the motor, the force sensor, the cartridge including the plunger, and a battery arranged to provide a current to the motor under control of a motor current driver.

Moreover, a computer program is proposed, which is configured to cause a processor executing the computer program to perform the actions of the proposed method.

Moreover, a computer readable medium is proposed, which is encrypted with such a computer program. The computer readable medium could be for instance a read only memory, a flash memory, a compact disc or any other kind of memory.

In more general terms, moreover an apparatus is proposed, which comprises means for receiving a signal from a force sensor, the signal representing a force that is applied by a motor, for example a stepper motor, of an injection device to a plunger of a cartridge, and means for causing a current to be applied to the motor, for example a stepper motor, which is related to the represented force. The means could be implemented at least partially in hardware or they could be functional modules of program code.

The invention proceeds from the consideration that the torque that has to be provided by the motor of an injection device depends on the force that is required to move a plunger in a cartridge. This force may depend for example on the backpressure of a liquid leaving the cartridge when the plunger is moved forward and on friction acting on the plunger. The force can be measured by means of a force sensor. Since the available torque at a motor depends primarily on the current that is applied to the motor, it is proposed to control the current that is applied to the motor depending on the measured force and thus on the currently required mechanical power. This may have the effect that only as much torque is made available as needed and taken off. As a result, less energy may be converted into heat and the power consumption of the injection device may be decreased. Certain embodiments of the proposed approach may thus enable an energy-efficient control of a motor. If the injection device draws power from a battery, the life-span of the battery may be lengthened.

Embodiments of the proposed approach may be seen as an alternative or supplement to the approach presented in document EP 0 481 376 A2. Compared to document EP 0 481 376 A2, certain embodiments of the proposed approach are moreover more flexible, since the operating cycle does not have to be split up into intervals which are mapped to marked rotation angles of the motor. Moreover, certain embodiments of the proposed approach are better suited to deal with variations between operating cycles. Certain embodiments of the proposed approach are furthermore suited to save more energy, since the provided current can be matched more closely to the actually required torque.

In contrast to the approach presented in document WO 2005/093533 A1, embodiments of the proposed approach may be used as well with injection devices employing a plunger in a cartridge for discharging a liquid substance instead of an infusion pump squeezing a plastic tube. Measuring the backpressure during an infusion as suggested in document WO 2005/093533 A1 is not suited to provide any information on the force that is required to move a plunger, for instance in view of static friction.

A motor current driver could be caused to apply a certain current to the motor by providing a suitable current control value to the motor current driver. Such a current control value may represent for example an absolute current that should be used, or an indication that the currently used current should be increased or decreased by certain amount. It could further be a digital value or an analog value. The current control value could be related to the signal of the force sensor in that it is computed based on the received signal representing the force using mathematical functions. Alternatively, it could be determined in any other way, for example by mapping the received signal representing the force to a current control value using a database or an electrical circuit.

The proposed approach can be used with any desired kind of motor, in particular with any kind of motor that provides a torque which depends on the amount of current applied to the motor and that allows taking off a load torque which is smaller than the torque made available by the motor. Such a motor could also be referred to as an excess torque producing motor or as a motor decoupling output torque from input current. Examples are a stepper motor and a switched reluctance motor.

In an exemplary embodiment of the proposed method, the current that is caused to be applied to the motor is a current that is required to enable the motor to apply the force represented by the signal from the force sensor to the plunger, incremented by a predetermined fixed value. In an exemplary embodiment of the proposed apparatus, the controller could be configured to cause a corresponding current to be applied to the motor. In an exemplary embodiment of the proposed computer program and computer readable medium, the computer program could be designed to cause a corresponding current to be applied to the motor.

In another exemplary embodiment of the proposed method, the current caused to be applied to the motor is a current that is required to enable the motor to apply the force represented by the signal from the force sensor to the plunger, incremented by a predetermined fraction of the represented force. In an exemplary embodiment of the proposed apparatus, the controller could be configured to cause a corresponding current to be applied to the motor. In an exemplary embodiment of the proposed computer program and computer readable medium, the computer program could be designed to cause a corresponding current to be applied to the motor.

Providing always a slightly higher available torque at the output of the motor than currently required for moving the plunger may ensure a reliable movement of the plunger. For example, a possibly upcoming increase in the required mechanical power can be taken into account this way. The proposed increment by a fixed value and the proposed increment by a fixed fraction are examples that may be used to this end and that can be implemented in a particularly easy manner.

The motor may apply a force to the plunger via a transmission, for instance a transmission comprising a piston rod.

For determining the force that is applied by the motor to the plunger, the force sensor may be arranged at various locations between motor and plunger.

In an exemplary embodiment of the proposed method, the method comprises measuring the force that is applied by the motor to the plunger of a cartridge by means of a force sensor that is integrated in the plunger. In an exemplary embodiment of the proposed apparatus, the apparatus could comprise the cartridge with the plunger, wherein the force sensor is integrated in the plunger and configured to measure the force that is applied by the motor to the plunger.

In another exemplary embodiment of the proposed method, the motor is configured to apply a force to the plunger by means of a piston rod, and the method further comprises measuring the force that is applied by the motor to the plunger by means of a force sensor that is either integrated in the piston rod or arranged between the piston rod and the plunger. In an exemplary embodiment of the proposed apparatus, the apparatus could further comprise the force sensor, the motor and a piston rod, the motor being configured to apply a force to the plunger by means of the piston rod, and the force sensor being configured to measure the force that is applied by the motor to the plunger, wherein the force sensor is either integrated in the piston rod or arranged between the piston rod and the plunger. These embodiments have the effect that in the case of exchangeable cartridges, it is not required to provide a new force sensor with each cartridge.

All of the proposed locations for the force sensor have the advantage that there is usually no relative movement between the plunger and an element interacting with the plunger. Thus, an implementation resulting in a reliable signal may in some cases be easier than with a force sensor arranged for instance between motor and transmission.

However, depending on the implementation the force sensor could also be arranged at any other suitable location, for instance between the motor and a piston rod or even at a location that does not lie between motor and plunger. A force sensor could be arranged for example between a cartridge holder holding the cartridge and another part of the apparatus, if the force applied by the motor to the plunger is reflected by a force that can be sensed at this location.

In an exemplary embodiment of the proposed method, the proposed apparatus, the proposed computer program and the proposed computer readable medium, the force sensor is a force sensitive resistor or a quantum tunneling composite (QTC) sensor. Both kinds of sensors require little space and exhibit a decreasing resistance with an increasing pressure applied to them. Force sensitive resistors are particularly accurate and suited to provide a value representing the absolute force over a sufficient range. Quantum tunneling composite sensors can reach lower resistance values than force sensitive resistors and are almost completely unsusceptible to corrosion and influences by humidity. A quantum tunneling composite sensor could use for example printable quantum tunneling composite ink, which allows measuring very small forces. It has to be noted, though, that the employed force sensor could equally be any other type of force sensor, for instance a piezoelectric sensor or a strain gauge.

It is to be understood that the features of any presented embodiment can be combined with the features of any other presented embodiment.

Exemplary embodiments of the invention will be described in more detail in the following with reference to drawings.

FIG. 2c is a schematic block diagram presenting a further exemplary variation of the injection pen of FIG. 1;

FIG. 2d is a schematic block diagram presenting a further exemplary variation of the injection pen of FIG. 1;

DETAILED DESCRIPTION OF AN EMBODIMENT OF THE INVENTION

Figure 1:
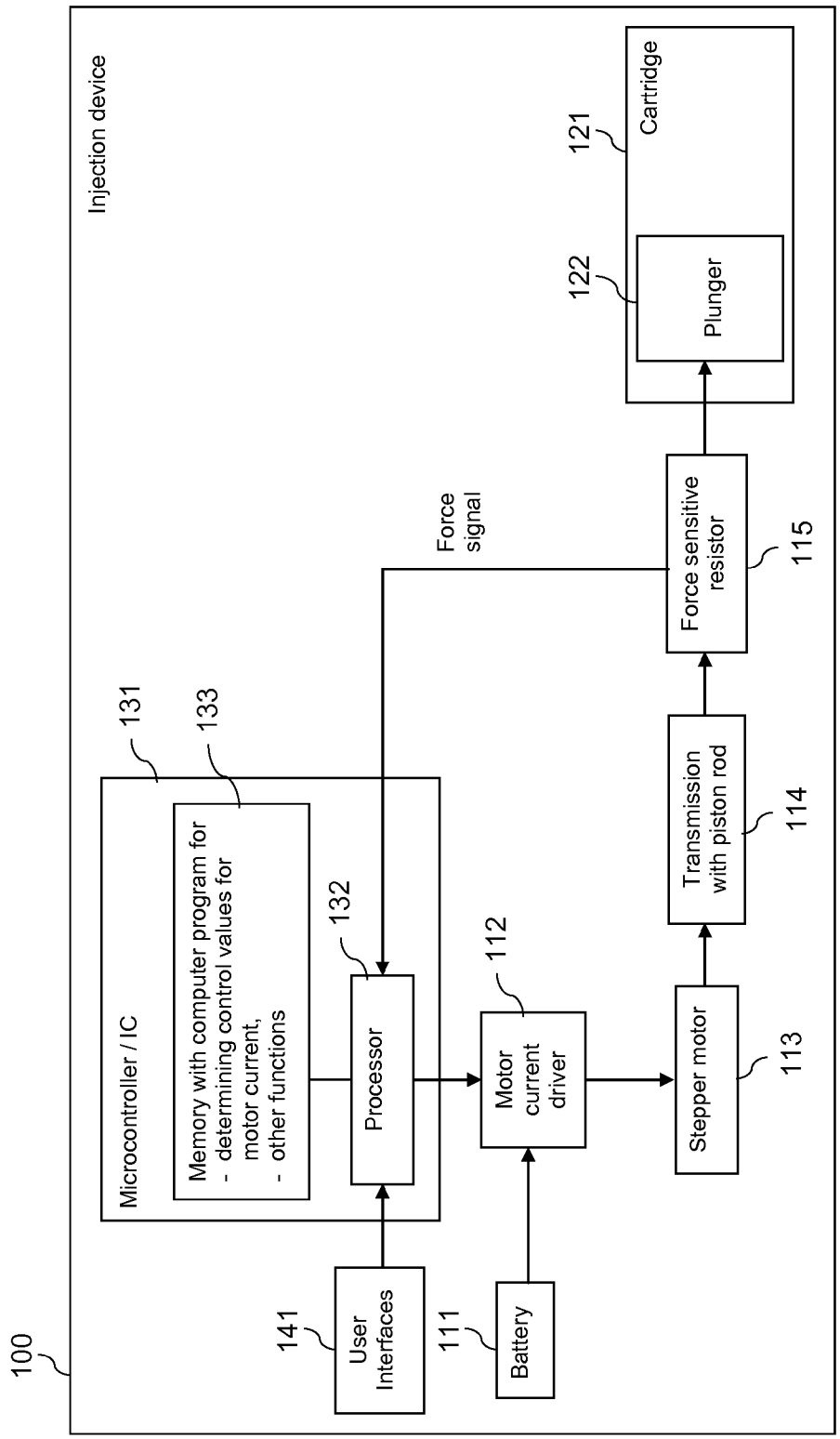
FIG. 1 is a schematic block diagram of an exemplary embodiment of an injection device.

FIG. 1 is a schematic block diagram, which presents an injection device or apparatus 100 with a motor control according to an exemplary embodiment of the invention.

The injection device 100 could be for instance an injection pen, such as an insulin pen or an injection pen for another medicament.

The injection device 100 may comprise a battery 111. The battery can be exchangeable or non-exchangeable. It can further be rechargeable or non-rechargeable.

The battery 111 is arranged to supply power to a motor current driver 112 of the injection device 100. The motor current driver 112 is linked to a motor, for example to a stepper motor 113 of the injection device 100. The stepper motor 113 interacts with a transmission 114 of the injection device 100. The transmission 114 may comprise for example a piston rod that is moved by the stepper motor 113. The transmission 114 may further comprise a transmissions gear or gearbox, for example to reduce the speed and increase the torque or force. The transmission 114 may further comprise a means to transfer a rotational movement of an axis of the motor 113 to a linear movement, such as a helical structure or screw thread running in a nut and/or the like.

The transmission 114 is arranged to act on a plunger 122. A force sensitive resistor 115 is arranged between the transmission 114 and the plunger 122, such that the force applied by the transmission 114 to the plunger 122 is also applied to the force sensitive resistor 115. The force sensitive resistor 115 is used as an exemplary force sensor. The force sensitive resistor 115 changes resistance when force is applied to its surface, with a known relation between force and resistance. The respective resistance can be detected via terminals of the resistor 115 provided to this end.

The plunger 122 is a part of a cartridge 121 filled with a liquid substance, for instance a medicament like insulin. By moving the plunger 122 in the cartridge 121 by a set amount, a corresponding amount of the liquid substance is forced out of the cartridge 121. The cartridge 121 may contain sufficient liquid substance for a plurality of applications.

If the injection device 100 is a durable pen, the cartridge 121 is replaceable. If the injection device 100 is pre-filled, the entire injection device 100 has to be discarded once the cartridge 121 is empty. Thus, the cartridge 121 may or may not be considered to belong to the injection device 100.

The force sensitive resistor 115 is linked to an interface of a processor 132 of a microcontroller 131 of the injection device 100. It is to be understood that there may be a direct link between the force sensitive resistor 115 and the processor 132 or an indirect link via some additional circuitry (not shown) which supports the detection of the resistance of the force sensitive resistor 115. The microcontroller 131 could be implemented for example in an integrated circuit (IC).

The processor 132 could be for instance a central processing unit (CPU). The processor 132 is configured to execute computer program code in order to cause the injection device 100 to perform certain actions. A memory 133 of the microcontroller 131 stores computer program code that may be retrieved by the processor 132. The computer program code in the memory 133 comprises code for determining a current control value. In addition, the memory 133 may comprise any further desired computer program code, for instance code for determining a number of steps by which the stepper motor 113 is to rotate and for determining a corresponding control value, as well as code for activating an injection cycle. In addition, a small random access memory (not shown) could be provided in microcontroller 131, for example for storing intermediate results.

A further interface of the processor 132 may be linked to a control input of the motor current driver 112. This link may be used by the processor 132 for example for causing the motor current driver 112 to energize coils of the stepper motor 113 in a sequence that results in a rotation of the shaft of the stepper motor 113 by a determined number of steps, and for causing the motor current driver 112 to apply a current to the energized coils of the stepper motor 113 in accordance with an exemplary embodiment of the invention, as will be described further below. At least a part of the motor current driver 112, for example a control logic part, may be integrated with the processor 132.

A further interface of the processor 132 may be linked to user interfaces 141 of the injection device 100. The user interfaces 141 may comprise for instance a dial for setting a dose that should be discharged by the injection device 100. The indicated value can be converted by the processor 132 into the required number of steps by which the stepper motor 113 should rotate. The user interfaces 141 may further comprise for instance a button for activating the discharge of the set dose. Furthermore, the user interface 141 may comprise a display for displaying information, such as a set dose, a battery status, and/or the like.

In the embodiment of FIG. 1, the stepper motor 113, the transmission 114 and the plunger 122 may be considered to be the controlled system of a closed loop.

The injection device 100 presented in FIG. 1 could be varied in many ways. For example, the microcontroller 131 could be one of a plurality of microcontrollers and take care exclusively of the current control. Other microcontrollers could then be provided for other functions. The injection device 100 could moreover comprise various alternative or additional interfaces connected to the processor 132, including for example a display, or a data interface enabling an exchange of data with other devices. The memory 133 or an additional memory could moreover store at least one database enabling a mapping of received values to control values, for example as a functional relationship, as a look-up table, and/or the like.

Some other variation options relating to the force sensitive resistor 115 are presented in the schematic block diagrams of FIGS. 2a to 2d.

Figure 2A:
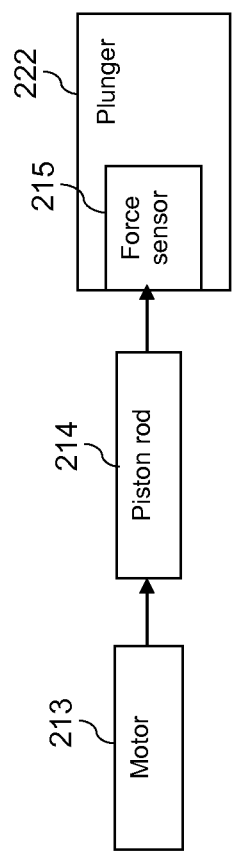
FIG. 2a is a schematic block diagram presenting an exemplary variation of the injection device of FIG. 1.

While FIG. 1 presents the force sensitive resistor 115 as a separate element arranged between the transmission 114 and the plunger 122, a force sensitive resistor 215 could also be integrated in the plunger 222 at the side of the plunger 222 facing a piston rod 214 of the transmission, as illustrated in FIG. 2a. Also in this case, the resistance of the force sensitive resistor 215 represents the force that is applied by a motor 213 to the plunger 222.

Figure 2B:
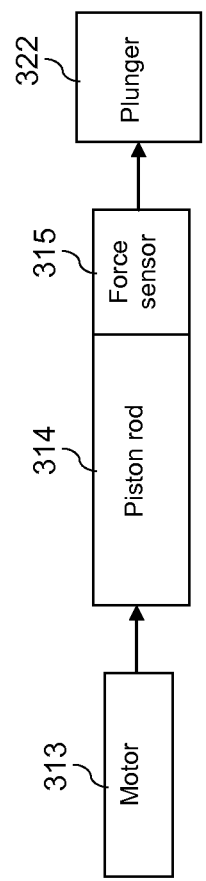
FIG. 2b is a schematic block diagram presenting a further exemplary variation of the injection pen of FIG. 1.

Further alternatively, a force sensitive resistor 315 could be integrated in a piston rod 314 of the transmission at the end of the piston rod 314 facing the plunger 322, as illustrated in FIG. 2b. Also in this case, the resistance of the force sensitive resistor 315 represents the force that is applied by a motor 313 to the plunger 322.

A further alternative is presented in FIG. 2c. Here, a cartridge 421 is shown to be located in a cartridge holder 423 and a force sensitive resistor 415 is arranged next to the cartridge holder 423 at a side opposite to a side at which a piston rod 414 enters the cartridge holder 423 to act on a plunger 422 in the cartridge 421. If the cartridge holder 423 is not fixed within the device, the force that is applied by a motor 413 to the plunger 422 via piston rod 414 is equivalent to the force with which the cartridge holder 423 is pressed to the casing of the injection device. Thus, the resistance of the force sensitive resistor 415 represents also in this case the force that is applied by a motor 413 to a plunger 422.

In a further example embodiment, the force sensitive resistor is arranged at a position where the motor is held in the casing of the injection device. The motor is pressed against the casing with a counter-force of an opposite direction, but substantially same amount as the force that is applied to the plunger. Thus, the resistance of the force sensitive resistor represents the force that is applied to the plunger.

Depending on the construction, a force sensitive resistor could also be arranged between the stepper motor and the transmission, as long as it can be ensured that the resistance of the force sensitive resistor represents the force that is applied by the stepper motor to a plunger. A further alternative is presented in FIG. 2d, where a force sensitive resistor 515 is arranged at the end of a piston rod 514 facing a motor 513. The motor 513 applies a force to the plunger 522 via the force sensitive resistor 515 and the piston rod 514, for example through a gearbox or transmission. The plunger 522 is illustrated again to be arranged in a cartridge 521 within a cartridge holder 523.

Figure 3:
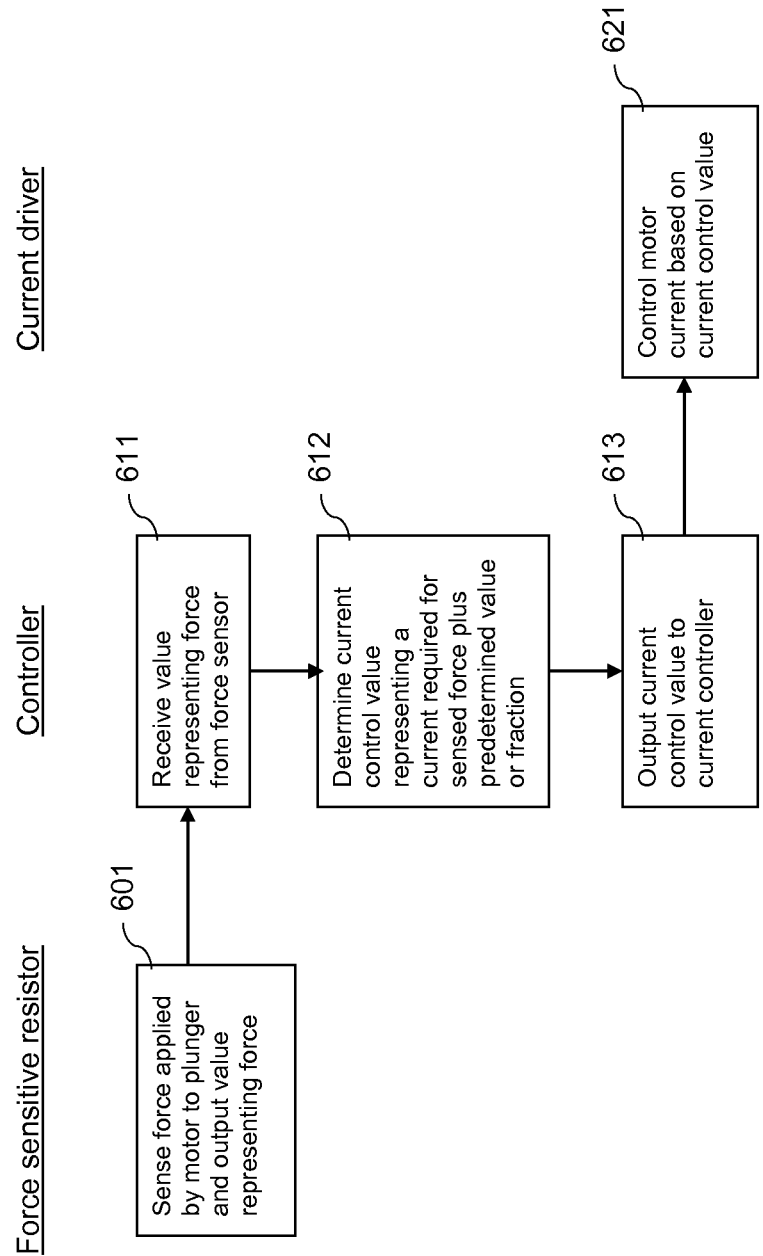
FIG. 3 is a flow chart illustrating aspects of an exemplary operation of the injection device of FIG. 1.

FIG. 3 is a flow chart illustrating aspects of an exemplary operation of the injection device 100 of FIG. 1.

On the left hand side the operation of the force sensitive resistor 115 is illustrated, in the middle an operation of the processor 132 is illustrated, and on the right hand side the operation of the motor current driver 112 is illustrated.

The force sensitive resistor 115 senses the force that is applied by the stepper motor 113 to the plunger 122 by changing its resistance accordingly. A value representing the current resistance and thus the currently applied force is provided to the processor 132. (action 601)

The processor 312 receives the value (action 611) and determines a current control value representing a current which is required for the sum of the represented force and a predetermined fixed value (action 612). Alternatively, the processor 312 could determine for example a current control value representing the current which is required for the sum of the represented force and a predetermined fraction of the represented force.

The processor 132 can determine the current control value computationally or by using a database that maps the value received from the force sensitive resistor 115 to a current control value. If a predetermined fixed value is to be used, a simple computation could be based for instance the equation $b=\lceil a \cdot y + x_1 \rceil$, where 'b' is the current control value, 'a' the value of the received signal, 'y' a factor mapping values representing a force to current control values and '$x_1$' a fixed value that is added to the current control value. The brackets $\lceil \ldots \rceil$ may represent a ceiling function. An alternative equation could be $b=\lceil (a+x_2) \cdot y \rceil$, where 'b' is the current control value, 'a' the value of the received signal, 'y' a factor mapping values representing a force to current control values and '$x_2$' a fixed value that is added to the value of the received signal. Thus, the value representing a force could be converted immediately into a current control value, which is then increased by a fixed value, or the value representing a force could first be increased by a fixed value before it is converted into a current control value. If a predetermined fraction is to be used instead, the equation $b=\lceil a \cdot y \cdot (1+x_3) \rceil$ could be used, where 'b' is the current control value, 'a' the value of the received signal, 'y' a factor mapping values representing a force to current control values and '$x_3$' a predetermined fraction, for instance 0.1 in order to achieve an increase of 10% of the current control value a*y.

The determined current control value is then provided by the processor 132 to the motor current driver (action 613).

The motor current driver 112 applies a current to the stepper motor 113, which corresponds to the current control value (action 621).

Thus, by determining and providing a current control value, the microcontroller 131 causes the motor current driver 112 to apply a current to the stepper motor 113, which is related to the signal from the force sensor 115.

It is to be understood that the processor 132 may provide additional control values to the motor current driver 112, for instance the control values indicated above.

Figure 4:
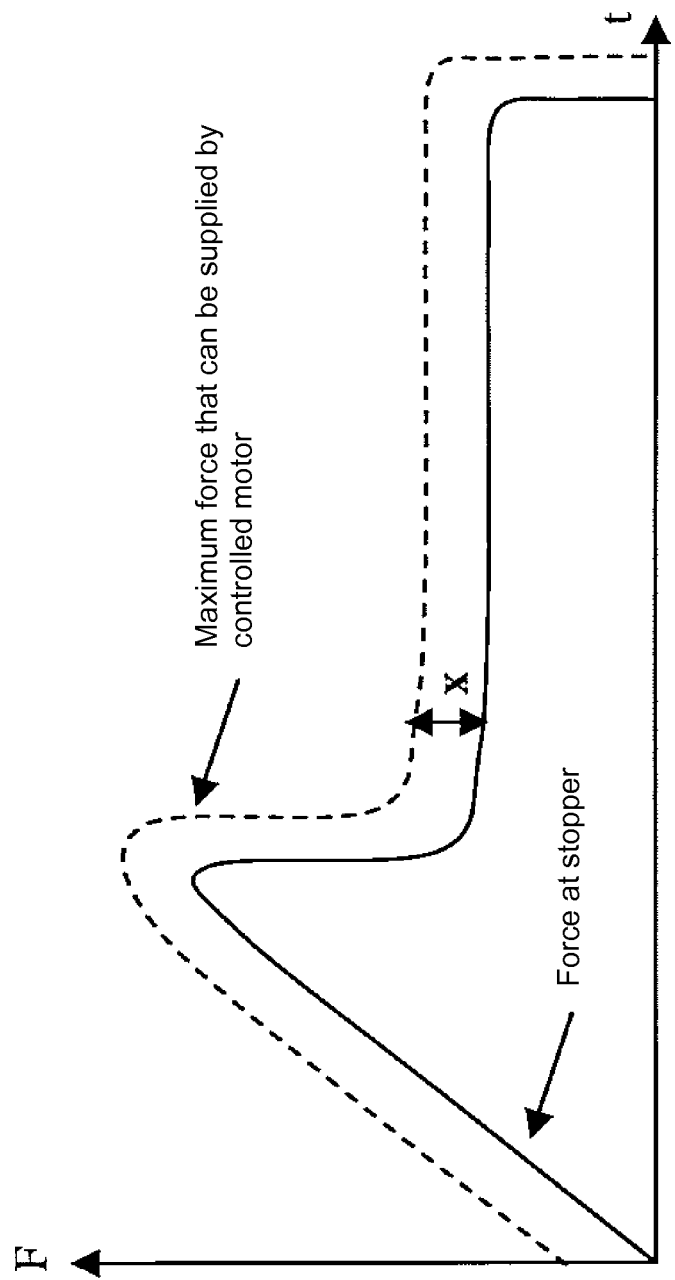
FIG. 4 is a diagram illustrating forces during an exemplary operation of the injection device of FIG. 1.

FIG. 4 is a diagram illustrating the effect of the presented current control.

The diagram depicts force (F) over time (t).

A solid line represents a force that is required to move the plunger 122 with a constant feed during a respective operating cycle. When the stepper motor 113 is started, the force at the plunger 122 rises, until static friction is overcome and the plunger 122 starts moving. As soon as the plunger 122 is in motion, a smaller force is required to complete the operating cycle and to discharge the desired dose of liquid substance. The force that is required to set the plunger 122 in motion may vary. It may depend for instance on the time of the last operating cycle, since in some cases, the plunger 122 may be moved less easily in the cartridge 121 after a longer period of non-use.

A dashed line represents the maximum force that could be applied by the stepper motor 113 with the presented current control. The force corresponds to the force at the plunger 122; it is only slightly lacking behind and increased by a value 'x'.

It can be seen that while it is ensured that a higher force is available than required so that the required motion is achieved in a reliable manner, there is only little unused energy that is converted into heat. Thus, the energy consumption is reduced and the life-span of the battery increased.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)$_5$-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)$_5$-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)$_5$-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2, H-(Lys)6-des Pro36, Pro37, Pro38 [Met(O)14, Asp28] Exendin-4(1-39)-NH2, H-Asn-(Glu)$_5$-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)$_5$ des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)$_5$-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)$_5$-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It is to be understood that the presented embodiments can be varied in many ways within the scope of the appended claims. In particular, all of the described components of the presented injection pump have only been selected by way of example, various components may be omitted or added, and any depicted link can be a direct link or an indirect link via some other components.

The invention claimed is:

1. A method comprising:
    receiving, by a controller, a signal from a force sensor, the signal representing a force that is applied by a stepper motor of an injection device to a plunger of a cartridge; and
    causing, by the controller, a current to be applied to the motor, which current is required to enable the motor to apply a force corresponding to a sum of the force represented by the signal from the force sensor and a predetermined value.

2. The method according to claim 1, wherein the predetermined value is a predetermined fixed value.

3. The method according to claim 1, wherein the predetermined value is a predetermined fraction of the represented force.

4. The method according to claim 1, comprising measuring the force that is applied by the motor to the plunger of a cartridge by means of a force sensor that is integrated in the plunger.

5. The method according to claim 1, wherein the stepper motor is configured to apply the force to the plunger by means of a piston rod, the method further comprising measuring the force that is applied by the motor to the plunger by means of a force sensor that is one of:
    integrated in the piston rod; and
    arranged between the piston rod and the plunger.

6. The method according to claim 1, wherein the force sensor is one of a force sensitive resistor, a quantum tunneling composite sensor and a strain gauge.

7. The method according to claim 1, wherein the cartridge comprises a first end closed by a septum which may be pierced by a needle and a second end closed by the plunger.

8. An apparatus comprising a controller,
    the controller being configured to receive a signal from a force sensor, the signal representing a force that is applied by a stepper motor of an injection device to a plunger of a cartridge; and
    the controller being configured to cause a current to be applied to the motor, which current is required to enable the motor to apply a force corresponding to a sum of the force represented by the signal from the force sensor and a predetermined value.

9. The apparatus according to claim 8, wherein the predetermined value is a predetermined fixed value.

10. The apparatus according to claim 8, wherein the predetermined value is a predetermined fraction of the represented force.

11. The apparatus according to claim 8, comprising the cartridge with the plunger, wherein the force sensor is integrated in the plunger and configured to measure the force that is applied by the motor to the plunger.

12. The apparatus according to claim 8, comprising the force sensor, the motor and a piston rod, the motor being configured to apply a force to the plunger by means of the piston rod, and the force sensor being configured to measure the force that is applied by the motor to the plunger, wherein the force sensor is one of:
    integrated in the piston rod;
    arranged between the piston rod and the plunger;
    arranged between the piston rod and the motor; and
    arranged between a cartridge holder holding the cartridge and another part of the apparatus.

13. The apparatus according to claim 8, wherein the force sensor is one of a force sensitive resistor, a quantum tunneling composite sensor and a strain gauge.

14. The apparatus according to claim 8, comprising the force sensor, the motor, the plunger and the cartridge.

15. The apparatus according to claim 8, wherein the apparatus is an injection device or an integrated circuit for an injection device.

16. The apparatus according to claim 8, wherein the cartridge comprises a first end closed by a septum which may be pierced by a needle and a second end closed by the plunger.

17. A non-transitory computer readable medium having instructions stored thereon that, if executed by a processor, cause the processor to perform operations comprising:
 receiving a signal from a force sensor, the signal representing a force that is applied by a stepper motor of an injection device to a plunger of a cartridge; and
 causing a current to be applied to the motor, which current is required to enable the motor to apply a force corresponding to a sum of the force represented by the signal from the force sensor and a predetermined value.

* * * * *